United States Patent
Nappa

(10) Patent No.: US 7,687,670 B2
(45) Date of Patent: Mar. 30, 2010

(54) COPRODUCTION OF HYDROFLUOROOLEFINS

(75) Inventor: Mario Joseph Nappa, Newark, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/281,666

(22) PCT Filed: Mar. 29, 2007

(86) PCT No.: PCT/US2007/008202

§ 371 (c)(1),
(2), (4) Date: Sep. 4, 2008

(87) PCT Pub. No.: WO2007/008202

PCT Pub. Date: Oct. 18, 2007

(65) Prior Publication Data

US 2009/0018375 A1     Jan. 15, 2009

(51) Int. Cl.
*C07C 17/00*     (2006.01)

(52) U.S. Cl. .................................................. 570/156

(58) Field of Classification Search ................ None
See application file for complete search history.

(56) References Cited

U.S. PATENT DOCUMENTS

| | | |
|---|---|---|
| 4,766,260 A | 8/1988 | Manzer et al. |
| 4,902,838 A | 2/1990 | Manzer et al. |
| 4,978,649 A | 12/1990 | Surovikin et al. |
| 5,136,113 A | 8/1992 | Rao |
| 5,268,122 A | 12/1993 | Rao et al. |
| 5,396,000 A | 3/1995 | Nappa et al. |
| 5,679,875 A | 10/1997 | Aoyama et al. |
| 6,369,284 B1 | 4/2002 | Nappa et al. |
| 6,540,933 B1 | 4/2003 | Sievert et al. |
| 6,548,719 B1 | 4/2003 | Nair et al. |
| 2006/0106263 A1 * | 5/2006 | Miller et al. ................ 570/155 |

FOREIGN PATENT DOCUMENTS

| | | |
|---|---|---|
| WO | 94/27940 A | 12/1994 |
| WO | 2007/019358 A | 2/2007 |
| WO | WO 2007/019358 * | 2/2007 |

OTHER PUBLICATIONS

International Search Report, dated Sep. 5, 2007.
Written Opinion of the International Searching Authority, dated Sep. 5, 2007.

* cited by examiner

*Primary Examiner*—Daniel M Sullivan
*Assistant Examiner*—Chukwuma O Nwaonicha

(57) ABSTRACT

Disclosed is a process for the co-manufacture of the hydrofluoroolefins HFC-1225ye and HFC-1234yf. The process comprises contacting a blend of 1,1,1,2,3,3-hexafluoropropane and 1,1,1,2,3-pentafluoropropane at a temperature of from about 200° C. to about 500° C. with a catalyst, optionally in the presence of an inert gas. The catalyst includes, but is not limited to, aluminum fluoride; fluorided alumina; metals on aluminum fluoride; metals on fluorided alumina; oxides, fluorides, and oxyfluorides of magnesium, zinc and mixtures of magnesium and zinc and/or aluminum; lanthanum oxide and fluorided lanthanum oxide; chromium oxides, fluorided chromium oxides, and cubic chromium trifluoride; carbon, acid-washed carbon, activated carbon, three dimensional matrix carbonaceous materials; and metal compounds supported on carbon. The metal compounds are oxides, fluorides, and oxyfluorides of at least one metal selected from the group consisting of sodium, potassium, rubidium, cesium, yttrium, lanthanum, cerium, praseodymium, neodymium, samarium, chromium, iron, cobalt, rhodium, nickel, copper, zinc, and mixtures thereof. The product hydrofluoroolefins are separated from unreacted hydrofluorocarbons and hydrogen fluoride. In another embodiment, the unreacted hydrofluorocarbons optionally may be recirculated back through the process.

10 Claims, No Drawings

COPRODUCTION OF HYDROFLUOROOLEFINS

BACKGROUND OF THE INVENTION

1. Field of the Invention

The present disclosure relates to the field of production and purification of hydrofluoroolefin compounds. This invention particularly relates to a method for the co-manufacture of 1,2,3,3,3-pentafluoropropene (FC-1225ye) and 2,3,3,3-tetrafluoropropene (FC-1234yf) via the catalytic dehydrofluorination of 1,1,1,2,3,3-hexafluoropropane and 1,1,1,2,3-pentafluoropropane.

2. Description of Related Art

Chlorine-containing compounds such as chlorofluorocarbons (CFCs) are considered to be detrimental to the Earth's ozone layer. Many of the hydrofluorocarbons (HFCs), used to replace CFCs, have been found to contribute to global warming. Therefore, there is a need to identify new compounds that do not damage the environment, but also possess the properties necessary to function as refrigerants, solvents, cleaning agents, foam blowing agents, aerosol propellants, heat transfer media, dielectrics, fire extinguishing agents, sterilants and power cycle working fluids. Fluorinated olefins, especially those containing one or more hydrogens in the molecule (referred to herein as hydrofluoroolefins) are being considered for use in some of these applications such as in refrigeration as well as in processes to make fluoropolymers. Blends of HFC-1225ye and HFC-1234yf are useful as refrigerant compositions which have lower potential to contribute to global warming than refrigerant compositions such as blends of HFC-134a. Particularly useful are blends for HFC-1225ye and HFC-1234yf which contain greater than 50% by weight of HFC-1225ye, which renders the blend nonflammable U.S. Pat. No. 6,369,284 describes a method for making HFC 1225ye or HFC 1225zc from HFC-236ea or HFC-236fa respectively by dehydrofluorination. U.S. Pat. No. 6,548,719 describes a method of dehydrohalogenating hydrofluorocarbons to produce hydrofluoroolefins such as HFC-1234ze using alkali metal hydroxides with phase transfer catalysts. U.S. Pat. Nos. 5,679,875 and 5,396,000 disclose a method for making HFC-1225ye from HFC-236ea via catalytic dehydrofluorination. Pending U.S. application Ser. No. 11/264, 183 discloses dehydrofluorination of hydrofluorocarbons to produce hydrofluoroolefins.

Blends of HFC-1225ye and HFC-1234yf are particularly useful as refrigerant compositions which have lower global warming potential than hydrofluorocarbons currently in use. It would be useful from a manufacturing perspective to be able to directly manufacture a desired blend in a single process instead of having to blend the two HFC's produced individually.

BRIEF SUMMARY OF THE INVENTION

In one embodiment, a process is provided for the co-manufacture of hydrofluoroolefins HFC-1225ye and HFC-1234yf. The process comprises contacting a blend of 1,1,1,2,3,3-hexafluoropropane and 1,1,1,2,3-pentafluoropropane at a temperature of from about 200° C. to about 500° C. with a catalyst, optionally in the presence of an inert gas. The catalyst includes, but is not limited to, aluminum fluoride; fluorided alumina; metals on aluminum fluoride; metals on fluorided alumina; oxides, fluorides, and oxyfluorides of magnesium, zinc and mixtures of magnesium and zinc and/or aluminum; lanthanum oxide and fluorided lanthanum oxide; chromium oxides, fluorided chromium oxides, and cubic chromium trifluoride; carbon, acid-washed carbon, activated carbon, three dimensional matrix carbonaceous materials; and metal compounds supported on carbon. The metal compounds are oxides, fluorides, and oxyfluorides of at least one metal selected from the group consisting of sodium, potassium, rubidium, cesium, yttrium, lanthanum, cerium, praseodymium, neodymium, samarium, chromium, iron, cobalt, rhodium, nickel, copper, zinc, and mixtures thereof. The product hydrofluoroolefins are separated from unreacted hydrofluorocarbons and hydrogen fluoride. In another embodiment, the unreacted hydrofluorocarbons optionally may be recirculated back through the process.

DETAILED DESCRIPTION OF THE INVENTION

This invention provides a process for the production of a blend of cis- and trans-1,2,3,3,3-pentafluoropropene (i.e., $CF_3CF=CHF$ or HFC-1225ye) (hereinafter referred to a simply as 1,2,3,3,3-pentafluoropropene, or HFC-1225ye) and 2,3,3,3-tetrafluoropropene (i.e., $CF_3CF=CH_2$ or HFC-1234yf) from 1,1,1,2,3,3-hexafluoropropane (i.e., $CF_3CHFCHF_2$ or HFC-236ea) and 1,1,1,2,3-pentafluoropropane (i.e., $CF_3CHFCH_2F$ or HFC-245eb). HFC-236ea and HFC-245eb can be readily prepared by known art methods. HFC-236cb for example can be readily prepared by hydrogenation of hexafluoropropene in the presence of a Pd/C catalyst.

In accordance with one embodiment of the invention, a blend of HFC-236ea and HFC-245eb is dehydrofluorinated, thereby forming a product mixture of HFC-1225ye and HFC-1234yf over a selected catalyst.

The dehydrofluorination of a hydrofluorocarbon may be carried out in the vapor phase. Vapor phase dehydrofluorination of a hydrofluorocarbon may be suitably carried out using typical dehydrofluorination catalysts. Generally, the present dehydrofluorination may be carried out using any dehydrofluorination catalyst known in the art. These catalysts include, but are not limited to, aluminum fluoride; fluorided alumina; metals on aluminum fluoride; metals on fluorided alumina; oxides, fluorides, and oxyfluorides of magnesium, zinc and mixtures of magnesium and zinc and/or aluminum; lanthanum oxide and fluorided lanthanum oxide; chromium oxides, fluorided chromium oxides, and cubic chromium trifluoride; carbon, acid-washed carbon, activated carbon, three dimensional matrix carbonaceous materials; and metal compounds supported on carbon. The metal compounds are oxides, fluorides, and oxyfluorides of at least one metal selected from the group consisting of sodium, potassium, rubidium, cesium, yttrium, lanthanum, cerium, praseodymium, neodymium, samarium, chromium, iron, cobalt, rhodium, nickel, copper, zinc, and mixtures thereof.

Dehydrofluorination catalysts include aluminum fluoride, fluorided alumina, metals on aluminum fluoride, and metals on fluorided alumina, as disclosed in U.S. Pat. No. 5,396,000, incorporated herein by reference. Fluorided alumina and aluminum fluoride can be prepared as described in U.S. Pat. No. 4,902,838, incorporated herein by reference. Suitable metals include chromium, magnesium (e.g., magnesium fluoride), Group VIIB metals (e.g., manganese), Group IIIB metals (e.g., lanthanum), and zinc. In use, such metals are normally present as halides (e.g., fluorides), as oxides and/or as oxyhalides. Metals on aluminum fluoride and metals on fluorided alumina can be prepared by procedures as described in U.S. Pat. No. 4,766,260, incorporated herein by reference. In one embodiment, when supported metals are used, the total metal content of the catalyst is from about 0.1 to 20 percent by weight, typically from about 0.1 to 10 percent by weight. Preferred catalysts include catalysts consisting essentially of aluminum fluoride and/or fluorided alumina.

Additionally, dehydrofluorination catalysts include oxides, fluorides, and oxyfluorides of magnesium, zinc and mixtures of magnesium and zinc and/or aluminum. A suitable catalyst may be prepared, for example by drying magnesium oxide until essentially all water is removed, e.g., for about 18 hours at about 100° C. The dried material is then transferred to the reactor to be used. The temperature is then gradually increased to about 400° C. while maintaining a flow of nitrogen through the reactor to remove any remaining traces of moisture from the magnesium oxide and the reactor. The temperature is then lowered to about 200° C. and a fluoriding agent, such as HF, or other vaporizable fluorine containing compounds such as HF, $SF_4$, $CCl_3F$, $CCl_2F_3$, $CHF_3$, $CHClF_2$ or $CCl_2FCClF_2$, optionally diluted with an inert gas such as nitrogen, is passed through the reactor. The inert gas or nitrogen can be gradually reduced until only HF or other vaporizable fluorine containing compounds is being passed through the reactor. At this point, the temperature can be increased to about 450° C. and held at that temperature to convert the magnesium oxide to a fluoride content corresponding to at least 40 percent by weight, e.g., for 15 to 300 minutes, depending on the fluoriding agent flowrate and the catalyst volume. The fluorides are in the form of magnesium fluoride or magnesium oxyfluoride; the remainder of the catalyst is magnesium oxide. It is understood in the art that fluoriding conditions such as time and temperature can be adjusted to provide higher than 40 percent by weight fluoride-containing material.

Another suitable procedure for the catalyst preparation is to add ammonium hydroxide to a solution of magnesium nitrate and, if present, zinc nitrate and/or aluminum nitrate. The ammonium hydroxide is added to the nitrate solution to a pH of about 9.0 to 9.5. At the end of the addition, the solution is filtered, the solid obtained is washed with water, dried and slowly heated to 500° C., where it is calcined. The calcined product is then treated with a suitable fluorine-containing compound as described above.

Yet another procedure for the preparation of metal (i.e., magnesium, optionally containing also zinc and/or aluminum) fluoride catalysts containing one or more metal fluorides is to treat an aqueous solution of the metal(s) halide(s) or nitrate(s) in deionized water with 48 percent aqueous HF with stirring. Stirring is continued overnight and the slurry evaporated to dryness on a steam bath. The dried solid is then calcined in air at 400° C. for about four hours, cooled to room temperature, crushed and sieved to provide material for use in catalyst evaluations.

Additionally, dehydrofluorination catalysts include lanthanum oxide and fluorided lanthanum oxide.

Suitable fluorided lanthanum oxide compositions may be prepared in any manner analogous to those known to the art for the preparation of fluorided alumina. For example, the catalyst composition can be prepared by fluorination of lanthanum oxide.

Suitable catalyst compositions may also be prepared by precipitation of lanthanum as the hydroxide, which is thereafter dried and calcined to form an oxide, a technique well known to the art. The resulting oxide can then be pretreated as described herein.

The catalyst composition can be fluorinated to the desired fluorine content by pretreatment with a fluorine-containing compound at elevated temperatures, e.g., at about 200° C. to about 450° C. The pretreatment with a vaporizable fluorine-containing compound such as HF, $SF_4$, $CCl_3F$, $CCl_2F_3$, $CHF_3$, $CHClF_2$ or $CCl_2FCClF_2$ can be done in any convenient manner including in the reactor which is to be used for carrying out the dehydrofluorination reaction. By vaporizable fluorine-containing compound is meant a fluorine containing compound which, when passed over the catalyst at the indicated conditions, will fluorinate the catalyst to the desired degree.

A suitable catalyst may be prepared, for example, by drying $La_2O_3$ until essentially all moisture is removed, e.g., for about 18 hours at about 400° C. The dried catalyst is then transferred to the reactor to be used. The temperature is then gradually increased to about 400° C. while maintaining a flow of $N_2$ through the reactor to remove any remaining traces of moisture from the catalyst and the reactor. The temperature is then lowered to about 200° C. and the vaporizable fluorine-containing compound is passed through the reactor. If necessary, nitrogen or other inert gases can be used as diluents. The $N_2$ or other inert diluents can be gradually reduced until only the vaporizable fluorine-containing compound is being passed through the reactor. At this point the temperature can be increased to about 450° C. and held at that temperature to convert the $La_2O_3$ to a fluorine content corresponding to at least 80 percent $LaF_3$ by weight, e.g., for 15 to 300 minutes, depending on the flow of the fluorine containing compound and the catalyst volume.

Another suitable procedure for the catalyst preparation is to add ammonium hydroxide to a solution of $La(NO_3)_3 6H_2O$. The ammonium hydroxide is added to the nitrate solution to a pH of about 9.0 to 9.5. At the end of the addition, the solution is filtered, the solid obtained is washed with water, and slowly heated to about 400° C., where it is calcined. The calcined product is then treated with a suitable vaporizable fluorine-containing compound as described above.

Additionally, dehydrofluorination catalysts include chromium oxides, fluorided chromium oxides, and cubic chromium trifluoride. Cubic chromium trifluoride may be prepared from $CrF_3 XH_2O$, where X is 3 to 9, preferably 4, by heating in air or an inert atmosphere (e.g., nitrogen or argon) at a temperature of about 350° C. to about 400° C. for 3 to 12 hours, preferably 3 to 6 hours.

Cubic chromium trifluoride is useful by itself, or together with other chromium compounds, as a dehydrofluorination catalyst. Preparation of cubic chromium trifluoride is described in U.S. Pat. No. 6,031,141, incorporated herein by reference. Of note are catalyst compositions comprising chromium wherein at least 10 weight percent of the chromium is in the form of cubic chromium trifluoride, particularly catalyst compositions wherein at least 25 percent of the chromium is in the form of cubic chromium trifluoride, and especially catalyst compositions wherein at least 60 percent of the chromium is in the form of cubic chromium trifluoride. The chromium, including the cubic chromium trifluoride can be supported on and/or physically mixed with materials such as carbon, aluminum fluoride, fluorided alumina, lanthanum fluoride, magnesium fluoride, calcium fluoride, zinc fluoride and the like. Preferred are combinations including cubic chromium trifluoride in combination with magnesium fluoride and/or zinc fluoride.

Additionally, dehydrofluorination catalysts include activated carbon, or three dimensional matrix carbonaceous materials as disclosed in U.S. Pat. No. 6,369,284, incorporated herein by reference; or carbon or metals such as sodium, potassium, rubidium, cesium, yttrium, lanthanum, cerium, praseodymium, neodymium, samarium, chromium, iron, cobalt, rhodium, nickel, copper, zinc, and mixtures thereof, supported on carbon as disclosed in U.S. Pat. No. 5,268,122, incorporated herein by reference. Carbon from any of the following sources are useful for the process of this invention; wood, peat, coal, coconut shells, bones, lignite, petroleum-based residues and sugar. Commercially available carbons which may be used include those sold under the following trademarks: Barneby & Sutcliffe™, Darco™, Nucharm, Columbia JXN™, Columbia LCK™, Calgon PCB, Calgon BPL™, Westvaco™, Norit™, and Barnaby Cheny NB™.

Carbon includes acid-washed carbon (e.g., carbon which has been treated with hydrochloric acid or hydrochloric acid followed by hydrofluoric acid). Acid treatment is typically sufficient to provide carbon that contains less than 1000 ppm of ash. Suitable acid treatment of carbon is described in U.S. Pat. No. 5,136,113, incorporated herein by reference. The carbon also includes three dimensional matrix porous carbonaceous materials. Examples are those described in U.S. Pat. No. 4,978,649, incorporated herein by reference. Of note are three dimensional matrix carbonaceous materials which are obtained by introducing gaseous or vaporous carbon-containing compounds (e.g., hydrocarbons) into a mass of granules of a carbonaceous material (e.g., carbon black); decomposing the carbon-containing compounds to deposit carbon on the surface of the granules; and treating the resulting material with an activator gas comprising steam to provide a porous carbonaceous material. A carbon-carbon composite material is thus formed.

The physical shape of the catalyst is not critical and may, for example, include pellets, powders or granules. Additionally, for catalysts supported on carbon, the carbon may be in the form of powder, granules, or pellets, or the like. Although not essential, catalysts that have not been fluorided may be treated with HF before use. It is thought that this converts some of the surface oxides to oxyfluorides. This pretreatment can be accomplished by placing the catalyst in a suitable container (which can be the reactor to be used to perform the reaction of the instant invention) and thereafter, passing HF over the dried catalyst so as to partially saturate the catalyst with HF. This is conveniently carried out by passing HF over the catalyst for a period of time (e.g., about 15 to 300 minutes) at a temperature of, for example, about 200° C. to about 450° C.

The catalytic dehydrofluorination may be suitably conducted at a temperature in the range of from about 200° C. to about 500° C., and, in another embodiment, from about 300° C. to about 450° C. The contact time is typically from about 1 to about 450 seconds, and, in another embodiment, from about 10 to about 120 seconds.

The reaction pressure can be subatmospheric, atmospheric or superatmostpheric. Generally, near atmospheric pressures are preferred. However, the dehydrofluorination can be beneficially run under reduced pressure (i.e., pressures less than one atmosphere).

The catalytic dehydrofluorination can optionally be carried out in the presence of an inert gas such as nitrogen, helium, or argon. The addition of an inert gas can be used to increase the extent of dehydrofluorination. Of note are processes where the mole ratio of inert gas to hydrofluorocarbon undergoing dehydrofluorination is from about 5:1 to about 1:1. Nitrogen is a preferred inert gas.

The reaction zone for catalyzed dehydrofluorination may be a reaction vessel fabricated from nickel, iron, titanium or their alloys, as described in U.S. Pat. No. 6,540,933, incorporated herein by reference. A reaction vessel of these materials (e.g., a metal tube) optionally packed with the metal in suitable form may also be used. When reference is made to alloys, it is meant a nickel alloy containing from about 1 to about 99.9 weight percent nickel, an iron alloy containing about 0.2 to about 99.8 weight percent iron, and a titanium alloy containing about 72 to about 99.8 weight percent titanium. Of note is the use of an empty (unpacked) reaction vessel made of nickel or alloys of nickel such as those containing about 40 weight percent to about 80 weight percent nickel, e.g., Inconel™ 600 nickel alloy, Hastelly™ C617 nickel alloy or Hastelly™ C276 nickel alloy.

When used for packing, the metal or metal alloys may be particles or formed shapes such as, for example, perforated plates, rings, wire, screen, chips, pipe, shot, gauze, or wool.

The product mixture resulting from the dehydrofluorination of the hydrofluorocarbon blends will contain hydrofluoroolefins, unreacted hydrofluorocarbons and hydrogen fluoride. The amount and the relative proportions of unreacted hydrofluorocarbons will depend upon the percent conversion achieved in the reaction, as well as the composition of the hydrofluorocarbon blend. Unreacted hydrofluorocarbons can be recirculated back to the reaction zone for production of additional HFC-1225ye and HFC-1234yf. The product HFC-1225ye and HFC-1234yf may be recovered from the reaction product, hydrogen fluoride, and unreacted hydrofluorocarbons by conventional procedures such as distillation.

In one embodiment, the ratio of fluorocarbons HFC-236ea and HFC-245eb fed to the reaction zone can be from about 10:1 to about 80:1. The ratio of the two fluorocarbons fed to the reaction zone will determine the ratio of HFC-1225ye to HFC-1234yf obtained from the product mixture. In another embodiment, the ratio of HFC-236cb and HFC-245eb fed to the reaction zone is from about 35:1 to about 80:1.

The following Examples are meant to illustrate the invention and are not meant to be limiting.

Example 1

Dehydrofluorination of $CF_3CHFCHF_2$ and $CF_3CHFCH_2F$ to $CF_3CF=CHF$ (E and Z Isomers) and $CF_3CF=CH_2$ Over Carbonaceous Catalyst A mixture of $CF_3CHFCHF_2$, $CF_3CHFCH_2F$ (mole ratio 30:1) and nitrogen are passed through the reactor as follows. A Hastelloy™ nickel alloy reactor (2.54 cm OD×2.17 cm ID×24.1 cm L) is charged with 14.32 g (25 mL) of spherical (8 mesh) three dimensional matrix porous carbonaceous material prepared substantially as described in U.S. Pat. No. 4,978,649, incorporated herein by reference. The packed portion of the reactor is heated by a 5"×1" ceramic band heater clamped to the outside of the reactor. A thermocouple positioned between the reactor wall and the heater measures the reactor temperature. After charging the reactor with the carbonaceous material, nitrogen (10 ml/min, $1.7×10^{-7}$ m$^3$/s) is passed through the reactor and the temperature is raised to 200° C. during a period of one hour and maintained at this temperature for an additional 4 hours. At a temperature of 350° C., 10 sccm of nitrogen ($1.7×10^{-7}$ m$^3$/s) and 15 sccm ($2.5×10^{-7}$ m$^3$/s) of a blend of $CF_3CHFCHF_2/CF_3CHFCH_2F$ are mixed and flowed through the reactor. The temperature is then raised to 400° C., and the flow rates held constant. The effluent for both temperatures is sampled and analyzed by $^{19}F$ NMR. A portion of the total reactor effluent is sampled on-line for organic product analysis using a gas chromatograph equipped with a mass selective detector (GC-MS); the results are summarized in Table 1. The bulk of the reactor effluent containing organic products and also inorganic acid, such as HF, is treated with aqueous caustic for neutralization

TABLE 1

| Temp., °C. | $N_2$ flow (sccm) | HFC flow (sccm) | Concentrations, (Mole %) | | |
|---|---|---|---|---|---|
| | | | $CF_3CF\!=\!CH_2$ | $CF_3CF\!=\!CHF$ | Unks |
| 350 | 10 | 15 | 57.8 | 39.2 | 3.0 |
| 400 | 10 | 15 | 55.5 | 37.7 | 6.8 |

Unks = unknowns

Example 2

Synthesis of $CF_3CF\!=\!CH_2$ and $CF_3CF\!=\!CHF$ with Fluorided Alumina

A 15 in (38.1 cm)×⅜ in (0.95 cm) Hastelloy tube is charged with 7.96 grams (13 cc) of gamma-alumina ground to 12-20 mesh (0.84 to 1.68 mm). The catalyst is activated by heating at 200° C. for 15 minutes under a nitrogen purge (50 sccm, $8.3 \times 10^{-7}$ m³/s). The temperature is raised to 325° C. for 10 minutes, to 400° C. for 20 minutes, and then lowered to 300° C. for 60 minutes. The nitrogen flow is reduced to 35 sccm ($5.8 \times 10^{-7}$ m³/s) and anhydrous HF vapor is fed at 12 sccm ($2.0 \times 10^{-7}$ m³/s) for 35 minutes. The temperature is then raised to 325° C. for 60 minutes, to 350° C. for 60 minutes, to 375° C. for 90 minutes, to 400° C. for 30 minutes, and to 425° C. for 40 minutes. The nitrogen flow is then reduced to 25 sccm ($4.2 \times 10^{-7}$ m³/s) and the HF raised to 20 sccm ($3.3 \times 10^{-7}$ m³/s) for 20 minutes. The nitrogen flow is then reduced to 15 sccm ($2.5 \times 10^{-7}$ m³/s) and the HF flow increased to 28 sccm ($4.7 \times 10^{-7}$ m³/s) for 20 minutes. The nitrogen flow is then reduced to 5 sccm ($8.3 \times 10^{-8}$ m³/s) and the HF increased to 36 sccm ($6.0 \times 10^{-7}$ m³/s) for 20 minutes. The nitrogen flow is then shut off, and the HF flow increased to 40 sccm ($6.7 \times 10^{-7}$ m³/s) for 121 minutes.

The temperature of the reactor is set to 400° C., and a mixture of 10 sccm ($1.7 \times 10^{-7}$ m³/s) of nitrogen and 15 sccm ($2.5 \times 10^{-7}$ m³/s) of various blends of $CF_3CHFCHF_2$ and $CF_3CHFCH_2F$ are passed through the reactor giving a contact time of 60 seconds. The flows are reduced to 5 sccm $8.3 \times 10^{-8}$ m³/s) of nitrogen (and 7.5 sccm ($1.3 \times 10^{-7}$ m³/s) of HFC giving a contact time of 120 seconds. The effluent is sampled under both sets of conditions and analyzed by $^{19}F$ NMR. The effluent compositions as determined by GC are listed in Table 2.

TABLE 2

| Temp., °C. | $N_2$ flow (sccm) | 236ea:245eb ratio | HFC Flow (sccm) | Concentrations, Mole % | | |
|---|---|---|---|---|---|---|
| | | | | $CF_3CF\!=\!CH_2$ | $CF_3CF\!=\!CHF$ | Unks |
| 400 | 5 | 10:1 | 7.5 | 85.6 | 11.9 | 2.5 |
| 400 | 5 | 30:1 | 7.5 | 58.0 | 39.3 | 2.7 |
| 400 | 5 | 50:1 | 7.5 | 44.3 | 54.2 | 1.5 |
| 400 | 5 | 80:1 | 7.5 | 30.2 | 68.6 | 1.2 |

Unks = unknowns

Example 3

Synthesis of $CF_3CF\!=\!CH_2$ and $CF_3CF\!=\!CHF$ with Fluorided Alumina

A 15 in (38.1 cm)×⅜ in (0.95 cm) Hastelloy tube was charged with 7.87 grams (13 cc) of gamma-alumina ground to 12-20 mesh (0.84 to 1.68 mm). The catalyst was activated by heating at 200° C. for 15 minutes under a nitrogen purge (50 sccm, $8.3 \times 10^{-7}$ m³/s). The temperature was raised to 325° C. for 10 minutes, to 400° C. for 20 minutes, and then lowered to 300° C. for 60 minutes. The nitrogen flow was reduced to 35 sccm ($5.8 \times 10^{-7}$ m³/s) and anhydrous HF vapor was fed at 12 sccm ($2.0 \times 10^{-7}$ m³/s) for 35 minutes. The temperature was then raised to 325° C. for 60 minutes, to 350° C. for 60 minutes, to 375° C. for 90 minutes, to 400° C. for 30 minutes, and to 425° C. for 40 minutes. The nitrogen flow was then reduced to 25 sccm ($4.2 \times 10^{-7}$ m³/s) and the HF raised to 20 sccm ($3.3 \times 10^{-7}$ m³/s) for 20 minutes. The nitrogen flow was then reduced to 15 sccm ($2.5 \times 10^{-7}$ m³/s) and the HF flow increased to 28 sccm ($4.7 \times 10^{-7}$ m³/s) for 20 minutes. The nitrogen flow was then reduced to 5 sccm ($8.3 \times 10^{-8}$ m³/s) and the HF increased to 36 sccm ($6.0 \times 10^{-7}$ m³/s) for 20 minutes. The nitrogen flow was then shut off, and the HF flow increased to 40 sccm ($6.7 \times 10^{-7}$ m³/s) for 121 minutes.

The temperature of the reactor was set to 375° C., and a mixture of 13 sccm ($2.2 \times 10^{-7}$ m³/s) of a blend of $CF_3CHFCHF_2$ and $CF_3CHFCH_2F$ in a 9:1 mole ratio were passed through the reactor giving a contact time of 60 seconds. The effluent compositions as determined by GCMS are listed in Table 3 below in mole %.

TABLE 3

| 1234yf | Z-1225ye | 1234ze | E-1225ye | 236ea | 245eb |
|---|---|---|---|---|---|
| 8.85 | 17.55 | 1.3% | 2.2% | 69.8% | 0.3% |

While specific embodiments of the invention have been shown and described, further modifications and improvements will occur to those skilled in the art. It is desired that it be understood, therefore, that the invention is not limited to the particular form shown and it is intended in the appended claims which follow to cover all modifications which do not depart from the spirit and scope of the invention.

What is claimed is:

1. A process for the co-manufacture of 1,2,3,3,3-pentafluoropropene and 2,3,3,3-tetrafluoropropene comprising:
   dehydrofluorinating a blend of 1,1,1,2,3,3-hexafluoropropane and 1,1,1,2,3-pentafluoropropane in a reaction zone having a catalyst, thereby forming a product mixture comprising said 1,2,3,3,3-pentafluoropropene and 2,3,3,3-tetrafluoropropene, unreacted hydrofluorocarbons and hydrogen fluoride, and separating said blend of 1,2,3,3,3-pentafluoropropene and 2,3,3,3-tetrafluoropropene from hydrogen fluoride and said unreacted hydrofluorocarbons to produce 1,2,3,3,3-pentafluoropropene and 2,3,3,3-tetrafluroropropene.

2. A process as in claim 1 further comprising recirculating the unreacted hydrofluorocarbons back to the reaction zone.

3. A process as in claim 1 wherein the process is carried out at a temperature of from 200° C. to 500° C.

4. A process as in claim 1 wherein the catalyst is selected from the group consisting of aluminum fluoride, fluorided alumina, and metals on fluorided alumina.

5. A process as in claim 4 wherein the catalyst is aluminum fluoride.

6. A process as in claim 1 wherein the process is carried out in the presence of an inert gas.

7. A process as in claim 6 wherein the inert gas is nitrogen.

8. A process as in claim 1 wherein the mole ratio of 1,1,1,2,3,3-hexafluoropropane and 1,1,1,2,3-pentafluoropropane fed to the reaction zone is from 10:1 to 80:1.

9. A process as in claim 8 wherein the mole ratio of 1,1,1,2,3,3-hexafluoropropane and 1,1,1,2,3-pentafluoropropane fed to the reaction zone is from 35:1 to 80:1.

10. A process as in claim 1 wherein the hydrofluoroolefins are separated from the hydrogen fluoride and the hydrofluorocarbons by distillation.

* * * * *